United States Patent [19]
Kotani et al.

[11] 4,002,486
[45] Jan. 11, 1977

[54] GLYOXAL COMPOSITION

[75] Inventors: Yasuo Kotani, Hirakata; Kunio Kageyama, Amagasaki, both of Japan

[73] Assignee: Nippon Gohsei Kagaku Kogyo Kabushiki Kaisha, Osaka, Japan

[22] Filed: Feb. 5, 1975

[21] Appl. No.: 547,269

Related U.S. Application Data

[63] Continuation-in-part of Ser. No. 434,339, Jan. 17, 1974, Pat. No. 3,912,529.

[30] Foreign Application Priority Data

| Feb. 1, 1973 | Japan | 48-13929 |
| July 9, 1973 | Japan | 48-77651 |
| July 13, 1973 | Japan | 48-79549 |

[52] U.S. Cl. ............................................. 106/213
[51] Int. Cl.² ........................................... C08L 3/02
[58] Field of Search ............................. 127/32, 33; 106/210–213, 187

[56] References Cited

UNITED STATES PATENTS

| 3,799,166 | 3/1974 | Marsan | 260/233.3 R |
| 3,912,529 | 10/1975 | Kotani et al. | 106/187 |

*Primary Examiner*—Theodore Morris
*Attorney, Agent, or Firm*—Armstrong, Nikaido & Wegner

[57] ABSTRACT

A non-fluid glyoxal composition prepared by admixing glyoxal, a water-soluble starch and water, in which the ratio of glyoxal and the water-soluble starch is in the range of about 1 : 2 to about 10 : 1 and water content is in the range of about 5 to about 40 % by weight in the composition, which is useful as a deodorant.

1 Claim, No Drawings

GLYOXAL COMPOSITION

CROSS-REFERENCES TO RELATED APPLICATION

This application is a continuation-in-part of application, Ser. No. 434,339 of Yasuo Kotani and Kunio Kageyama filed on Jan. 17, 1974 and now U.S. Pat. No. 3,912,529.

BACKGROUND OF THE INVENTION

The present invention relates to a novel nonfluid glyoxal composition comprising glyoxal, a water-soluble starch and water in the specific ratio, and more particularly relates to a glyoxal composition which maintains a form of non-sticky, non-hygroscopic powder in spite of large glyoxal content and shows similar chemical properties to those of an aqueous solution of glyoxal.

Glyoxal has been widely employed in various uses such as starting materials for organic reagents, finishing agents for fibers or paper, deodorant, soil stabilizer, and the like. In general, glyoxal is manufactured from ethylene or acetaldehyde by oxidation reaction, and usually it is obtained in the market as an aqueous solution not more than 40 % by weight. It is extremely difficult to concentrate an aqueous solution of glyoxal to more than 40 % by weight by a conventional process, such as evaporation or spray drying, since the aqueous solution becomes to highly viscous to form polyglyoxal.

On the other hand, it has been known that polyglyoxal is obtained in a form of powder. However, polyglyoxal is not so advantageous, because it is expensive for the complicated manufacturing and difficult to handle due to its hygroscopic property.

If it becomes possible to obtain cheaply glyoxal in high concentration, it can be expected that the cost for transportation will be decreased and novel use and application will be developed. Further, if it becomes possible to obtain the non-fluid glyoxal, for instance, in a form of block, pellet or powder, it also can be expected that novel use and application differing from a conventional aqueous solution of glyoxal will be developed.

There has been disclosed in U.S. Pat. No. 2,549,177 a composition comprising starch, glyoxal and water. However, the ratio of glyoxal and starch in this composition is 1 : 50 to 1 : 20 and the composition is in liquid, differing from the composition of the present invention.

There has also been known from U.S. Pat. No. 2,999,032 a process for preparing a clear, stable true solution of amylose, or of mixtures of amylose and amylopectin by dissolving amylose or the mixture in aqueous formaldehyde solution or aqueous glyoxal solution. However, a non-fluid composition is not disclosed in this patent relating to the amylose solutions containing formaldehyde or glyoxal, and the solution of this patent is different from the composition of the present invention.

OBJECTS OF THE INVENTION

It is an object of the present invention to provide a novel non-fluid glyoxal composition.

Another object of the invention is to provide a jellied glyoxal composition.

A further object of the invention is to provide a solidified glyoxal composition.

A more further object of the invention is to provide a process for preparing a solidified glyoxal composition by simple means.

A still further object of the invention is to provide novel applications for glyoxal.

These and other objects of the invention will become apparent from the description hereinafter.

DESCRIPTION OF THE INVENTION

It has now been found that the above-mentioned objects are accomplished because of discovering the fact that an aqueous solution of glyoxal loses its fluidity when a water-soluble starch is dissolved into the solution in the specific ratio to glyoxal.

In the present invention, the term "non-fluid" means that the present glyoxal composition is not in a form of liquid, i.e. is in a form of jelly or solid.

According to the present invention, it is essential that the ratio of glyoxal and a water-soluble starch should be in the range of about 1 : 2 to about 10 : 1 by weight, especially about 1 : 1 to about 10 : 1 by weight, and water is in the range of about 5 to about 40 % by weight in the composition, and these components should be homogeneously admixed. A composition containing glyoxal with less than the above ratio remains in liquid form as shown in the above-mentioned U.S. patents. The composition containing water of more than about 40 % by weight is a viscous liquid even if the ratio of glyoxal to the water-soluble starch is within the above-mentioned range. It is impossible to reduce the water content in the composition to less than 5 % by weight because glyoxal per se is apt to hydrate. The composition containing water in an amount which is less than about 40 % by weight, especially less than about 25 % by weight in the composition is a solid material which is neither hygroscopic nor sticky. The composition of such a solid type can also be molded into a desired form such as powder, granule, pellet or block. Especially, the composition having the water content of less than about 25 % by weight can become a very fine powder.

When the glyoxal composition of the present invention is put in water, glyoxal is eluted from the composition and the water-soluble starch in the composition is gradually dissolved in water. Therefore, there is not a bit of difference between chemical properties of the aqueous solution obtained from the present composition and those of a conventional aqueous solution of glyoxal. It is not too much to say that the glyoxal composition is solid glyoxal since a content of the water-soluble starch is very small and the composition can be handled as glyoxal without any trouble.

Examples of the water-soluble starch are soluble starch, oxidized starch, hydroxyethyl starch, acetate starch, phosphate starch, cationized starch, and the like. These water-soluble starches can be employed alone or as a mixture.

According to the present invention, the glyoxal composition is prepared by adding the water-soluble starch or an aqueous solution thereof to an aqueous solution of glyoxal (commercially sold) in the specific ratio to glyoxal as mentioned above and admixing them homogeneously. The mixture is jellied only by uniformly admixing them at any temperature. In case of employing the water-soluble starch in a solid form such as powder, the heating is efficient to shorten the period for preparing a uniform composition. For the purpose of preparing the composition of less water content, it is a practical method to dehydrate the composition having a larger water content by a conventional method, such as heating under a normal or reduced pressure. For example, it is practically impossible to prepare the composition having the ratio of glyoxal : water-soluble starch = 1 : 1 and the water content of 25 % by weight by means of directly admixing of the glyoxal solution and the water-soluble starch as long as a concentrated glyoxal solution more than 40 % by weight can not be obtained.

The glyoxal composition of solid type is prepared by drying the composition of jelly type. The composition of solid type obtained in a form of block can be readily crushed into fine powder. Also, the composition of solid type in a desired form such as powder, granule or pellet can be obtained by molding the composition of jelly type into a desired mold and drying it.

In accordance with the necessity, the composition of the invention can be added with additives, in a required quantity, such as dyestuff, pigment, surface active agent, filler, perfume, antiseptic, germicide, and the like.

The composition of the invention contains glyoxal in a high concentration and is basically applicable to the same uses as in a conventional glyoxal solution. However, since the composition has the non-fluidity, modified applications can be developed.

One embodiment of the present composition can be utilized as a deodorant of new type. When the composition is put into water which has a bad odor because of the presence of such compounds as ammonia, amines, hydrogen sulfide or mercaptans, the glyoxal in the composition elutes gradually into the water and the deodorant effect can be maintained for a longer period than in case of glyoxal solution.

The powdery composition containing glyoxal in the ratio of more than one part by weight to one part by weight of the water-soluble starch and water of less than about 25 % by weight, contains glyoxal in so extremely high concentration and has large surface area that the composition has the good effect on deodorizing even in air by contacting with it.

The powder composition can be employed as a deodorant for wrapping paper. When the paper making is carried out in the presence of the powdery composition, the paper obtained can contain glyoxal in high yield in comparison with employing a conventional aqueous solution of glyoxal. Thus obtained paper does not lose the flexibility and is useful for wrapping paper which encloses materials emitting bad odors such as fish, shell or meat. In case of employing the composition as a deodorant, the effect can be increased by adding perfumes such as coumarin, vanillin, Eau de Cologne, geranyl crotonate or lauryl methacrylate, glyoxylic acid, malic acid, citric acid, and the like.

The present invention is more particularly described and explained by means of the following illustrative Examples, in which all percentages are by weight except as noted.

EXAMPLE 1

A kneader having a capacity of one liter, which was maintained at a temperature of 90° to 95° C., was charged with 100 g. of soluble starch, 240 g. of 40 % aqueous solution of glyoxal and 160 g. of water, and was agitated. After 10 minutes from the charging, the mixture changed into a translucent jelly. The agitation was further continued, and when 282 g. of water was evaporated the agitation was stopped to give white powders consisting of 44 % of glyoxal, 46 % of soluble starch and 10 % of water.

EXAMPLE 2

In the same manner as Example 1, 150 g. of soluble starch, 250 g. of 40 % aqueous solution of glyoxal and 100 g. of water were uniformly admixed with agitation. After 10 minutes from the charging, the mixture changed to a jelly form. The agitation was further continued, and stopped at a point of time when 116 g. of water was evaporated to give white powders consisting of 26 % of glyoxal, 39 % of soluble starch and 35 % of water.

EXAMPLE 3

In the same manner as Example 1, 25 g. of oxidized starch, 190 g. of 40 % aqueous solution of glyoxal and 285 g. of water were uniformly admixed with agitation. After 10 minutes from the charging, the mixture changed to a transparent viscous liquid. The agitation was further continued, and stopped at a point of time when 375 g. of water was evaporated to give white powders consisting of 60 % of glyoxal, 20 % of oxidized starch and 20 % of water.

EXAMPLE 4

In the same manner as Example 1, 50 g. of hydroxyethyl starch and 450 g. of 40 % aqueous solution of glyoxal were uniformly admixed with agitation. After 10 minutes from the charging, the mixture changed to a transparent jelly form. The agitation was further continued, and stopped at a point of time when 140 g. of water was evaporated to give white powders consisting of 50 % of glyoxal, 14 % of hydroxyethyl starch and 36 % of water.

EXAMPLE 5

In the same manner as Example 1, 75 g. of hydroxyethyl starch and 425 g. of 40 % aqueous solution of glyoxal were uniformly admixed with agitation. After 10 minutes from the charging, the mixture changed to a transparent jelly form. The agitation was further continued, and stopped at a point of time when 152 g. of water was evaporated to give white powders consisting of 52 % of glyoxal, 23 % of hydroxyethyl starch and 25 % of water.

EXAMPLE 6

The white powder obtained in Example 1 was spread all over the bottom of a cylindrical vessel having a diameter of 46 cm. and a height of 60 cm. in an amount of 100 g. Then, ammonia gas was introduced into the vessel in a concentration of about 80 p.p.m. and the vessel was immediately sealed. After allowing to stand for 24 hours at a temperature of 20° C., the vessel was opened but there was no smell.

In order to compare the deodorizing effect, the same test as the above was repeated except that 100 g. of powdery active carbon was employed instead of the white powder of the invention. However, the strong smell of ammonia remained in the vessel.

EXAMPLE 7

A mixture consisting of 40 parts by weight of the white powder obtained in Example 2, 40 parts by weight of powdery active carbon and 20 parts by weight of bleaching powder was spread all over the bottom of the same cylindrical vessel as employed in Example 6. Then a plate was fixed in the vessel and 300 g. of a mixture of guts, head and bone of ray was put on the plate. The vessel was immediately sealed and allowed to stand for 24 hours at a temperature of 25° to 30° C. There was no unpleasant smell.

EXAMPLE 8

The white powder obtained in Example 3 was packed in a cotton bag in an amount of 500 g., and the bag was fixed in a water tank of a water-closet being capable of intermittently flushing. The water-closet was controlled by a syphon so as to drain away at intervals of about 30 minutes and each time the composition was put in water. As a result, unpleasant smell in a toilet room disappeared and its deodorizing effect lasted for 9 days.

EXAMPLE 9

To 50 g. in dry weight of kraft pulp were added 2.5 g. of the powdery composition obtained in Example 3 and 16.6 liters of water, and then the mixture was agitated to disperse uniformly. A TAPPI standard sheet machine (20 cm. × 25 cm.) was charged with 1 liter of the obtained dispersion, and thereto 10 liters of water was further added to form a sheet. Then the obtained sheet was dried to give a paper having a basis weight of 60 g./m.$^2$. A 78.8 % of the employed composition was fixed to the paper.

Thus obtained paper was put into the syringe filled with ammonia gas at 20° C. The amount of ammonia adsorbed in the paper was 2,333 ml./m.$^2$, while that in the blank paper was 1,380 ml./m.$^2$.

What is claimed is:

1. A powdery composition consisting essentially of glyoxal, at least one water-soluble starch selected from the group consisting of soluble starch, oxidized starch, hydroxyethyl starch, acetate starch, phosphate starch, and cationized starch, and water; the ratio of glyoxal and the water-soluble starch being in the range of about 1:2 to about 10:1 and water being in the range of about 5 to about 25 percent by weight in the composition.

* * * * *